United States Patent [19]
Price

[11] Patent Number: 6,007,240
[45] Date of Patent: Dec. 28, 1999

[54] METHOD AND APPARATUS FOR MODULATED-TEMPERATURE THERMOMECHANICAL ANALYSIS

[75] Inventor: Duncan M. Price, Exmall, United Kingdom

[73] Assignee: TA Instruments, Inc., New Castle, Del.

[21] Appl. No.: 09/059,581

[22] Filed: Apr. 14, 1998

[51] Int. Cl.[6] .................................................. G01N 25/00
[52] U.S. Cl. .............................................. 374/55; 374/56
[58] Field of Search ........................................ 374/55, 56

[56] References Cited

U.S. PATENT DOCUMENTS

| | | | |
|---|---|---|---|
| 3,474,658 | 10/1969 | Levy et al. | 374/56 |
| 4,019,365 | 4/1977 | Woo . | |
| 5,009,512 | 4/1991 | Lessi et al. | 374/56 |
| 5,224,775 | 7/1993 | Reading et al. . | |
| 5,248,199 | 9/1993 | Reading . | |
| 5,474,385 | 12/1995 | Reading . | |
| 5,710,426 | 1/1998 | Reed et al. . | |
| 5,826,983 | 10/1998 | Nakamura et al. | 374/55 |

FOREIGN PATENT DOCUMENTS

| | | | |
|---|---|---|---|
| 366744 | 12/1992 | Japan | 374/55 |
| 1063898 | 4/1967 | United Kingdom . | |

OTHER PUBLICATIONS

Chen, D. Dollimore., "Sinusoidal Temperature Treatments in Thermal Analysis," Thermochimica Acta 272, (1996): pp. 75–85.

Claudy, P., Commerceron, J.C. and Letoffe, J.M. "Quasi–State Study of Glass Transition of Glycerol by DSC", Termochimica acta (1988): pp. 251–260.

Flynn, Joseph "Thermodynamic Properties from Differential Scanning Calorimetry by Calorimetric Methods", Thermachimica Acta 8, (1974): pp. 69–81.

Haworth, B., Dong, Z. W., Davidson, P. "Characterisation of Shrinkage in Oriented PET Films and Containers by Thermomechanical Analysis (TMA)", (1993): pp. 325–335.

Jaffe, M. "Fibers", Thermal Characterization of Polymeric Materials, (1981): pp. 731–750.

Kiss, G., Seybold, K., and MIesel, T. "Error Analysis in Thermal Purity Determinations", H.G. Weidermann: Thermal Analysis, Proceedings of the Sixth International Conference on Thermal Analysis, Bayreuth, FRG, Birkhauser, Verlag, Basel, (1980): pp. 87–92.

Ozawa, Takeo "A New Method of Analyzing Thermogravimetric Data", vol. 38, No. II (Nov. 1965): pp. 1881–1886.

Paulik, F. "Special Trends in Thermal Analysis", John Wiley & Sons, Chichester (1975).

Paulik, F., Paulik, J. "Quasi–isothermal Thermodilatometry", Journal of Thermal Analysis, vol. 16 (1979): pp. 399–406.

Paulik J., Paulik, F., Arnild, M. "Derivatograph–C: Microcomputer Automated Equipment for Simultaneous TG.DTGG.DTA.EGA. and TD", Thermochimica Acta, 107 (1986): pp: 375–378.

Price, Duncan M. "Novel Methods of Modulated–Temperature Thermal Analysis", Thermochimica Acta, (1998): pp. 11–18.

Price, Duncan M. "Modulated–TemperatureThermomechanical Analysis", Journal of Thermal Analysis, (1998): pp. 231–236.

Reading, M., "ModulatedDifferential Scanning Calorimetry—A New Way Forward in Materials Characterization", Trends in Polymer Science, Aug. 1993, vol. 1: pp. 248–253.

(List continued on next page.)

*Primary Examiner*—Diego Gutierrez
*Assistant Examiner*—Maria Fernandez
*Attorney, Agent, or Firm*—Crowell & Moring LLP

[57] ABSTRACT

By employing a "modulated-temperature" heating program composed of a series of heat-isotherm stages, it is possible to separate the change in dimensions of an oriented material during heating into two contributions: a thermally "reversing" component which is due to linear thermal expansion and a "non-reversing" part arising from relaxation to the disordered state on heating above $T_g$. Some preliminary results for biaxially drawn poly(ethylene terephthalate) film are presented.

22 Claims, 14 Drawing Sheets

TMA SCHEMATIC (EXTENSION)

OTHER PUBLICATIONS

Reading, M., "Controlled Rate Thermal analysis and Beyond", Thermal Analysis–Techniques and Applications: pp. 127–155 No Date.

Resien, R., Widdman, G. and Truttmann, R., "Alternating Thermal Analysis Techniques", Thermochimica Acta, 272 (1996) pp. 27–39.

Sorensen O. Toft, "Densification Studies of Ceramic Powder Compacts by Quasi–Isothermal Dilatometry:", Riso National Laboratory, (1980): pp. 231–236.

Sorensen O. Toft, "Quasi–Isothermal Methods in Thermal Analysis", Thermochimica Acta, 50 (1982) : pp. 163–175.

Staub, H., Perron, W. "A New Method of Purity Determination by Means of Calorimetric Differential Thermal Analysi", Analytical Chemistry, 46 (1974): pp. 128–130 No Date.

Trznadek, M., Kryszewski, M. "Thermal Shrinkage of Oriented Polymers",(1992):pp. 259–301.

TAC '97 : The Second UK National Thermal Analysis and Calorimetry Symposium, (1997) pp: 14–15.

METHOD AND APPARATUS FOR MODULATED-TEMPERATURE THERMOMECHANICAL ANALYSIS

BACKGROUND

1. Field of the Invention

The present invention relates to thermomechanical analysis (TMA). TMA is a thermal analysis technique in which mechanical properties of a sample of a material are measured as a function of temperature.

2. Background of the Invention

Thermomechanical analysis can be performed using a variety of experimental configurations, including an extension configuration (shown in FIG. 1) and a compression configuration (shown in FIG. 2). Additional configurations for thermomechanical analyzers are well-known to those of skill in the art.

The present invention also relates to Modulated-Temperature DSC (MT-DSC). MT-DSC is a modification of differential scanning calorimetry, in which an oscillating heating rate is superimposed on a conventional linear temperature heating ramp. MT-DSC is described in an article by M. Reading, Trends in Polymer Science., vol. 1, page 248 (1993) and in U.S. Pat. No. 5,224,775 (the "'775 patent", which is incorporated herein by reference). In MT-DSC, the response of the differential heat flow signal (dQ/dt) to the heating rate (dT/dt) is given by:

$$\frac{dQ}{dt} = C_p \frac{dT}{dt} + f(t, T) \quad (1)$$

where $C_p$ is the sample's heat capacity and $f(t,T)$ represents heat flow associated with kinetically limited processes due to physical or chemical changes in the sample that occur both with time and temperature, as explained in Reading's Polymer Science article and disclosed in the '775 patent. The $f(t,T)$ term represents the "non-reversing" heat flow. Thermal events such as crystallization, evaporation, degradation, cross-linking etc. are non-reversing events, that would contribute to the non-reversing term. In MT-DSC the heat capacity of the sample is calculated by deconvoluting the measured heat flow signal into component signals. A sinusoidal temperature modulation is the most commonly applied program, although both saw-tooth and stepwise isothermal programs have been employed.

At present, modulated-temperature programs have only been used in differential scanning calorimeters, although Chen and Dollimore have considered the theoretical implications of using a sinusoidal heating rate in simultaneous DSC-TG (D. Chen and D. Dollimore, Thermochim. Acta, vol. 272, p. 75 (1996)).

SUMMARY OF THE INVENTION

Equations similar to the equation for MT-DSC (equation 1) can be written for TMA. For example, in a TMA configured to measure the length of a sample, when the sample is subjected to a modulated temperature program, the rate of change of sample length with respect to time (dL/dt), can be divided into two components:

$$\frac{dL}{dt} = \alpha \frac{dT}{dt} + f'(t, T) \quad (2)$$

where $\alpha$ is the thermal expansion coefficient (dL/dT and $f'(t,T)$ represents changes in length which occur due to relaxation of stresses in the sample or deformation under the applied load in the case of TMA. Previous studies by O. T. Sorensen, "Densification Studies of Ceramic Powder Compacts by Quasi-Isothermal Dilatometry", in H. G. Wiedemann (Ed.), THERMAL ANALYSIS, Proc. 6th ICTA, Vol. 1, Bayreuth, FRG, Birkhäuser Verlag, Basel 1980, p. 231–236, used stepwise-isothermal dilatometry to study the time and temperature dependence of the sintering of inorganic oxides. The duration of every isothermal stage was controlled by the rate of change of sample length. Thus this method forms part of the family of Controlled Rate Thermal Analysis techniques described in M. Reading, "Controlled Rate Thermal Analysis and Beyond," in E. L. Charsley & S. B. Warrington (Eds.), THERMAL ANALYSIS—TECHNIQUES & APPLICATIONS, The Royal Society of Chemistry, Cambridge, p. 127–155 (1992).

The nature of reversible and non-reversible length changes on heating for oriented polymers is described in the article by M. Jaffe; "Fibers", Chapter 7, in E. A. Turi (Ed.), THERMAL CHARACTERIZATION OF POLYMERIC MATERIALS, Academic Press, Orlando, pp.731–750 (1981). Whilst all materials generally have a positive coefficient of volume expansion, the inherent anisotropy of ordered polymer chains means that the linear thermal expansion coefficient along the chain axis may be negative. Furthermore, the metastable nature of most oriented polymer structures results in relaxation to the disordered state on heating above $T_g$, hence any change in specimen length with temperature will not be reversible until structural equilibrium is achieved. Trznadel & Drysewski describe this in a review of thermal shrinkage of oriented polymers in J. Macromol. Science—Rev. Macrom. Chem. Phys., vol. C32, p. 259 (1992). Thermal expansion is reversible (even if the sign of the coefficient of thermal expansion is negative) but any shrinkage is permanent, since it results in an increase in entropy due to loss of order in the matrix.

DETAILED DESCRIPTION OF THE INVENTION

Figure 1:
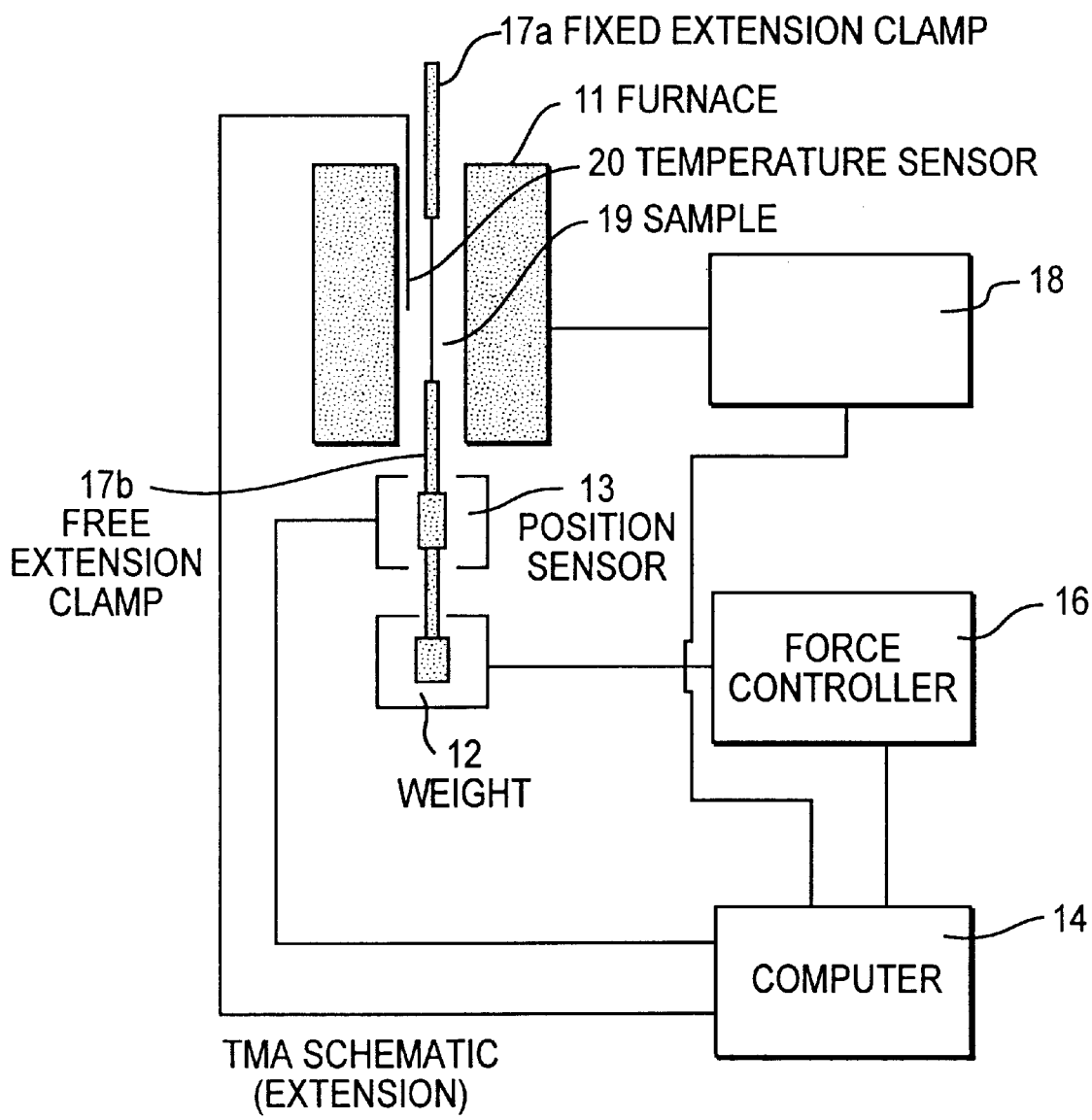
FIG. 1 is a schematic drawing of a thermomechanical analyzer according to the first embodiment of the present invention, in the extension configuration.
Figure 2:
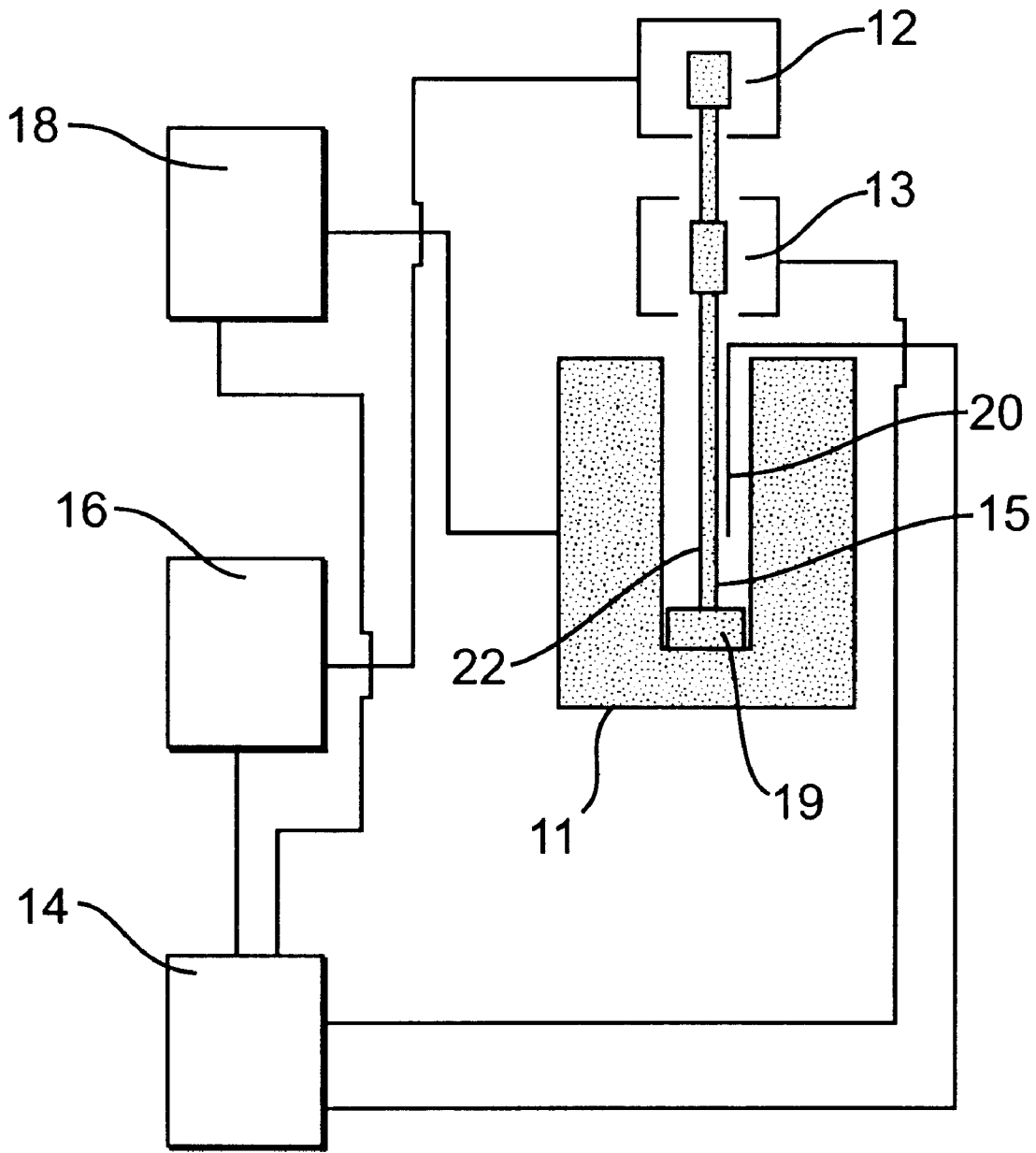
FIG. 2 is a schematic drawing of a thermomechanical analyzer according to the first embodiment of the present invention, in the compression configuration.

The first embodiment of the present invention may be practiced using a conventional thermomechanical analyzer, shown in FIG. 1 (a TMA configured in the extension mode) and FIG. 2 (a TMA configured in the compression mode).

FIG. 1 shows a conventional thermal analyzer comprising a furnace 11, a means for exerting a force on a sample (a motor or a weight) 12, a position sensor 13, a data station (such as a computer) 14, a force controller 16, a fixed extension clamp 17a and a free extension clamp 17b, and a temperature sensor (such as a thermocouple) 20. Operated in the conventional mode, the TMA of FIG. 1 measures the thermal expansion coefficient of sample as a function of temperature, but cannot distinguish between reversible and non-reversible effects. Operated according to the present invention, the temperature of the sample is increased using a temperature program that can be characterized as having an underlying rate of change modulated by a modulation function. The change in the length of the sample and the temperature of the sample are measured by position sensor 13, as the sample is subjected to the modulated temperature program. The temperature and change in length of the sample are recorded and stored in computer 14, and the resulting data is deconvoluted using the method described in U.S. Pat. No. 5,474,385.

FIG. 2 is a schematic diagram of a conventional thermomechanical analyzer in the compression configuration. In this configuration, all the components of the analyzer are the same, but the sample 19 is placed on a hard surface, and a rod 22 is pressed against the sample. Rod 22 is preferably a material, such as a silica rod, that is hard compared to the hardness of the sample. As the viscoelastic properties of the sample change as a function of temperature, rod 22 presses more (or less) deeply into the sample. Position sensor 13 detects the position of the rod, which is representative of the viscoelastic properties of the sample. The data from position sensor 13 is recorded and stored in computer 14, and is deconvoluted according to the method described in U.S. Pat. No. 5,474,385.

Figure 3:
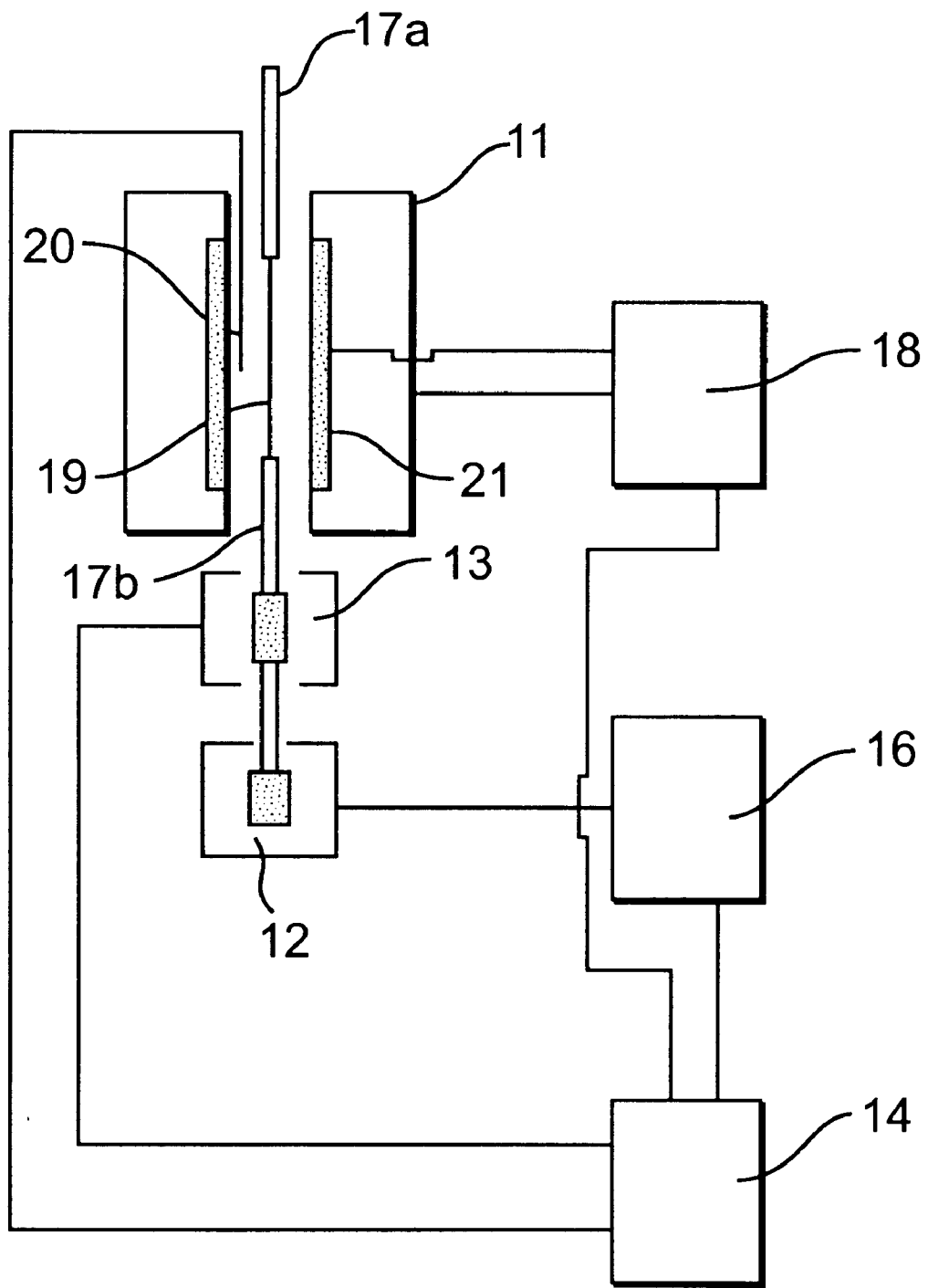
FIG. 3 is a schematic drawing of a thermomechanical analyzer according to the second embodiment of the present invention, in the extension configuration.
Figure 4:
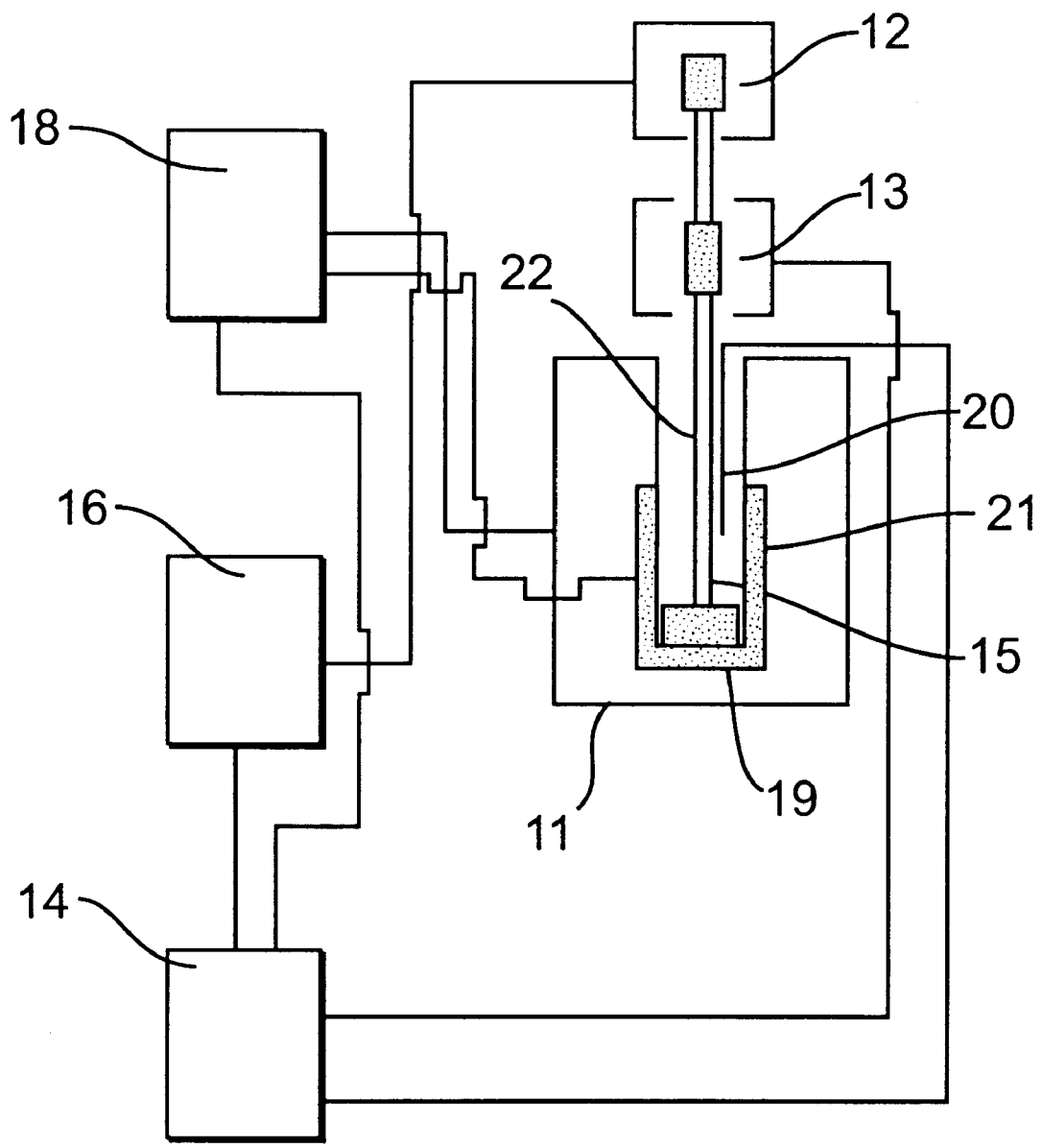
FIG. 4 is a schematic drawing of a thermomechanical analyzer according to the second embodiment of the present invention, in the compression configuration.

The second embodiment of the present invention uses a modified thermomechanical analyzer, shown in FIGS. 3 and 4. The apparatus of FIGS. 3 and 4 are similar to the apparatus of FIGS. 1 and 2, respectively, except that two furnaces are used. The main furnace 11 is used to control the average temperature of the sample (i.e., the average temperature over one modulation cycle), and the temperature modulation furnace 21 is used to provide the temperature modulation. The use of a special modulation furnace allows the apparatus to use modulation programs having higher frequencies than would be possible using the conventional apparatus.

The present invention will be illustrated with three examples. All the measurements described in the examples were carried out using the apparatus of the first embodiment of the invention, i.e., a conventional thermomechanical analyzer (a Shimadzu TMA-50), but they could have also been carried out using the apparatus of the second embodiment of the invention. The third example describes a calibration method that can be used to improve the quantitative accuracy of the present invention.

EXAMPLE 1

Figure 5:
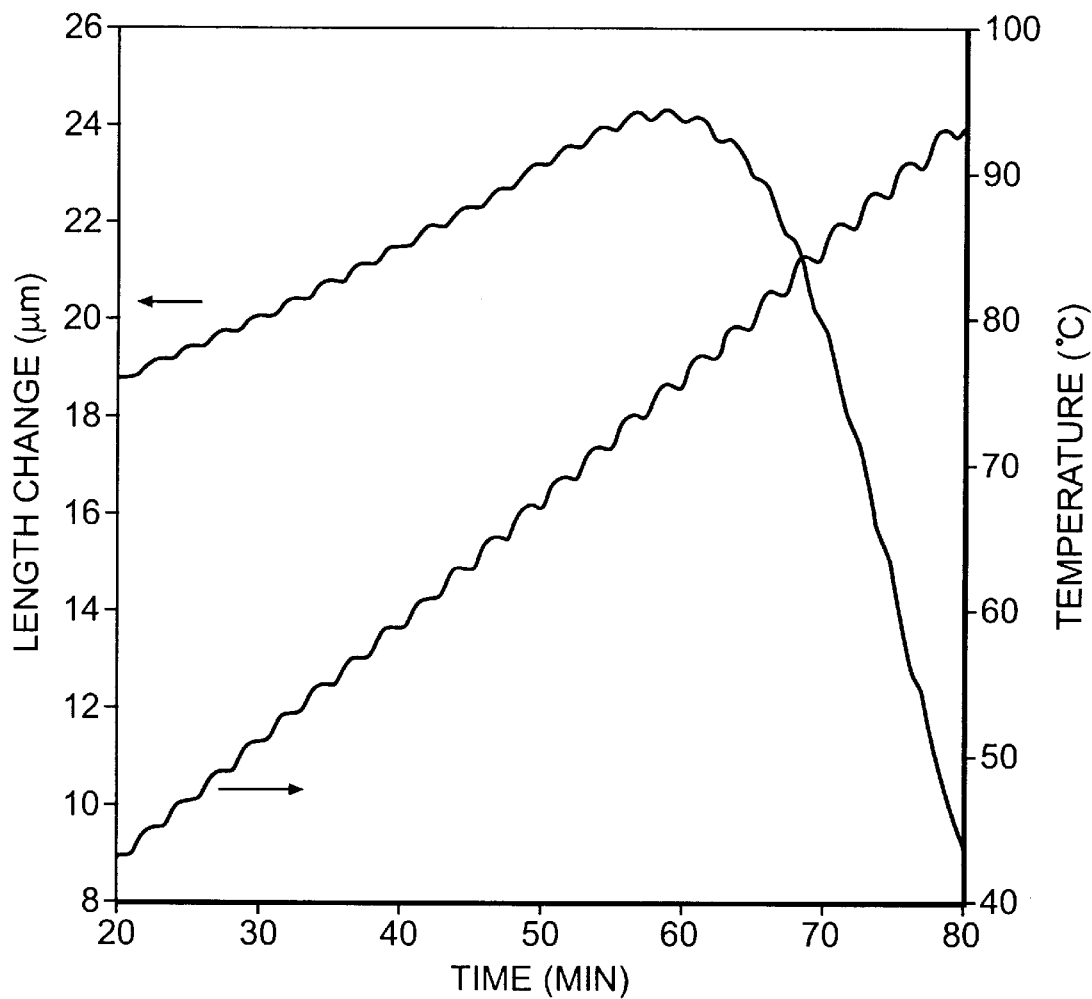
FIG. 5 is a plot of the raw length expansion (left-hand axis) and temperature (right-hand axis) as a function of time.
Figure 6:
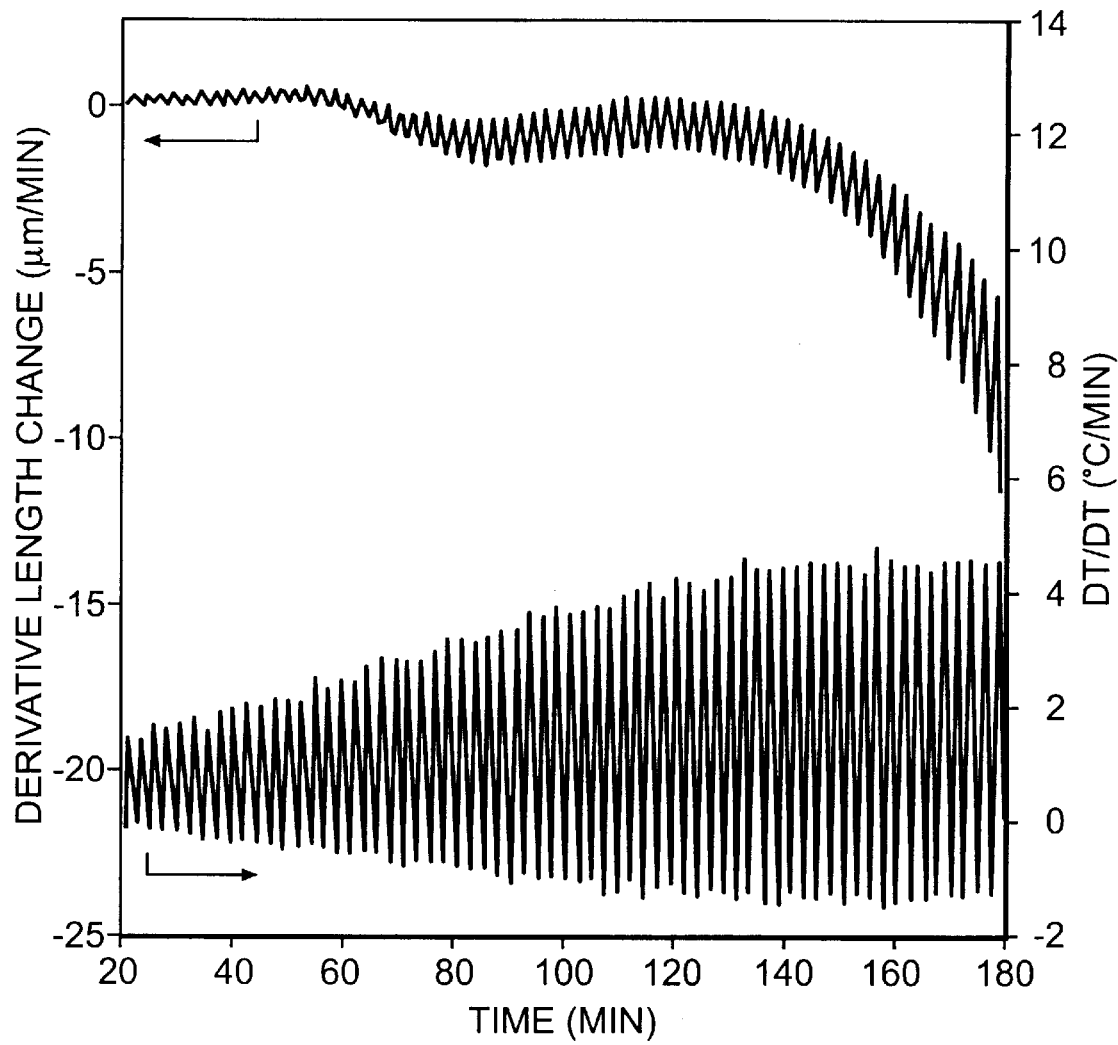
FIG. 6 is a plot of the first derivative of length change and temperature vs. time calculated from raw data.
Figure 7:
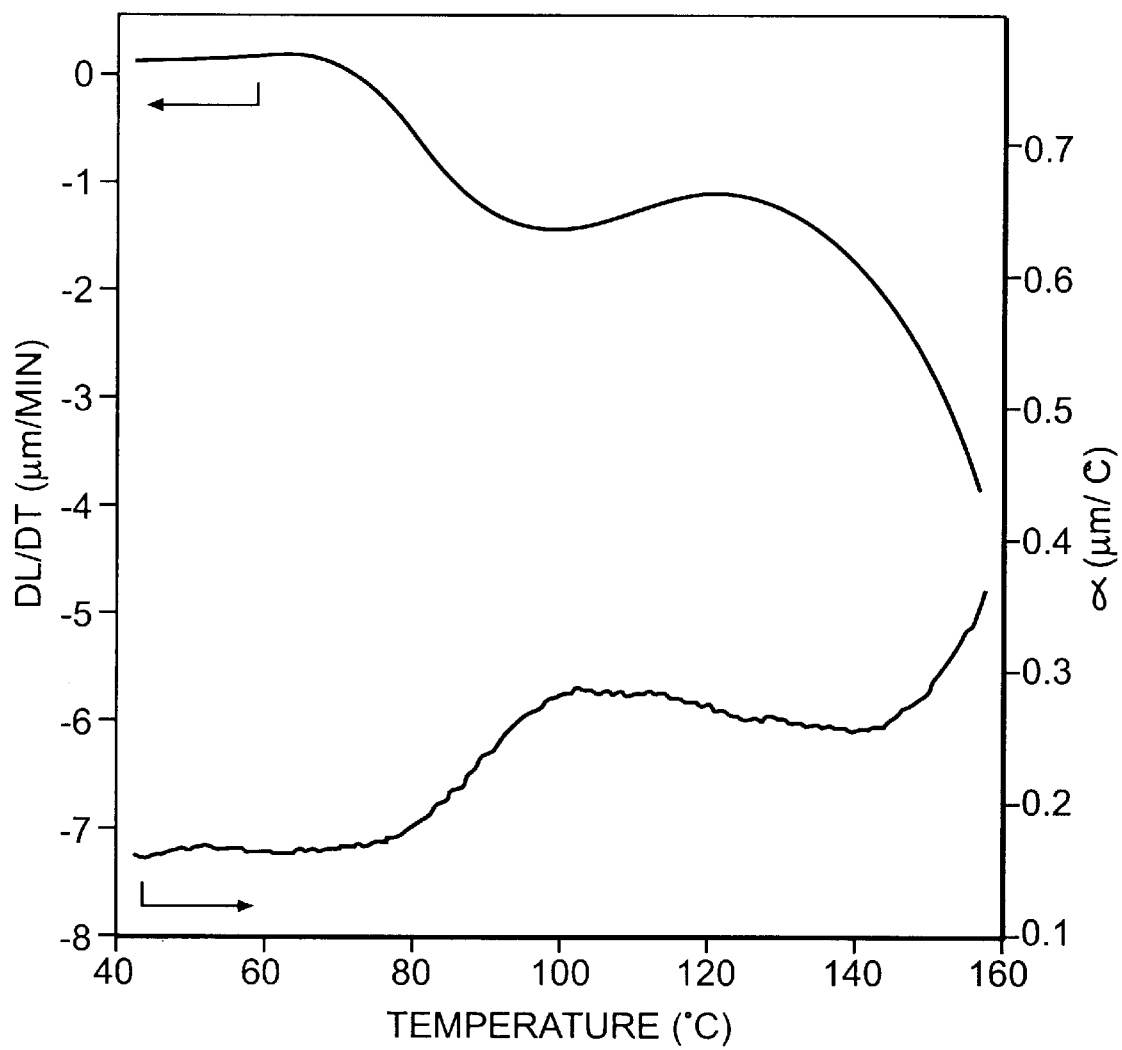
FIG. 7 is a plot of the data from FIG. 6, after deconvolution, showing the underlying rate of change of sample length (dL/dt) and the contribution from thermal expansion ($\alpha$).

The first example uses the TMA in the extension configuration shown in FIG. 1. A sample of 125 micron thick poly(ethylene terephthalate) film PET (Melinex®, ICI) was mounted in the film extension clamps under a 1 g load (too low to cause appreciable creep of the specimen at high temperature (B. Howarth, Z. W. Doug and P. Davidson, Polym. Int. vol. 32, p. 325 (1993)). Initial sample dimensions were 5 mm wide and 10 mm long. Measurements were started at 30° C. followed by a succession of heat/isotherm stages which served to raise the furnace temperature by 2° C. at 5° C. min$^{-1}$ followed by 2 min isotherm until 180° C. was reached. Sample length change and temperature were recorded by a computer every second. Some of the raw data from the instrument for PET film tested along the transverse axis to direction of manufacture is shown in FIG. 5. FIG. 5 shows the raw length change and temperature data from instrument (specimen expansion is shown in a positive direction). The first derivatives of the length change and temperature (dT/dt) curves are shown in FIG. 6. The heating rate oscillates about a mean value of 0.83° C. min$^{-1}$ within a 2.4 min period and, although the amplitude increased during the experiment due to overshoot of the temperature controller, the data can be deconvoluted by the method disclosed in U.S. Pat. No. 5,474,385 to Reading, which is incorporated herein by reference, in order to calculate the average time, temperature, rate of length change (dL/dt), thermal expansion coefficient (α) for each cycle according to Equation (2), as shown in FIG. 7.

Figure 8:
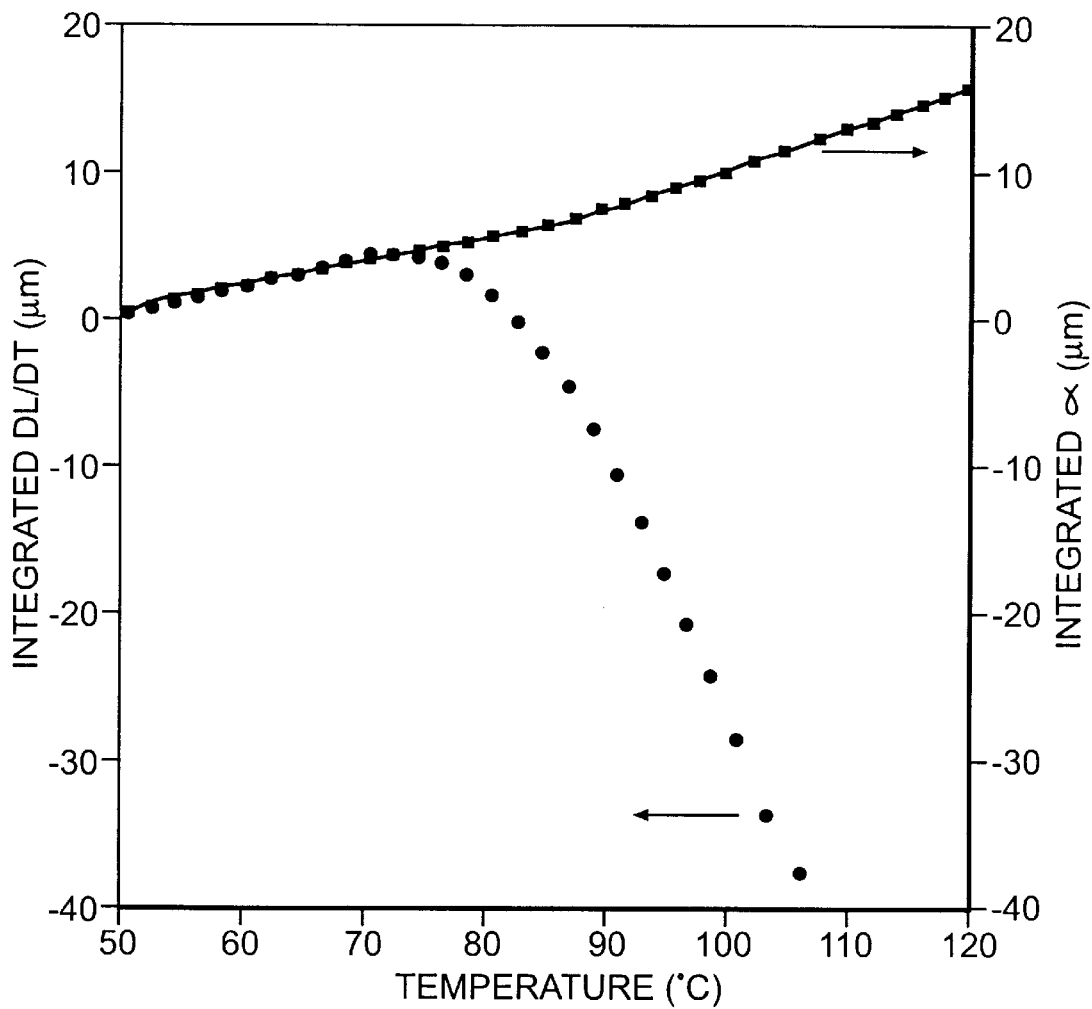
FIG. 8 is a plot of the cumulative integrals of dL/dt (with respect to time) and $\alpha$ (with respect to temperature) in region from 50 to 120° C.
Figure 9:
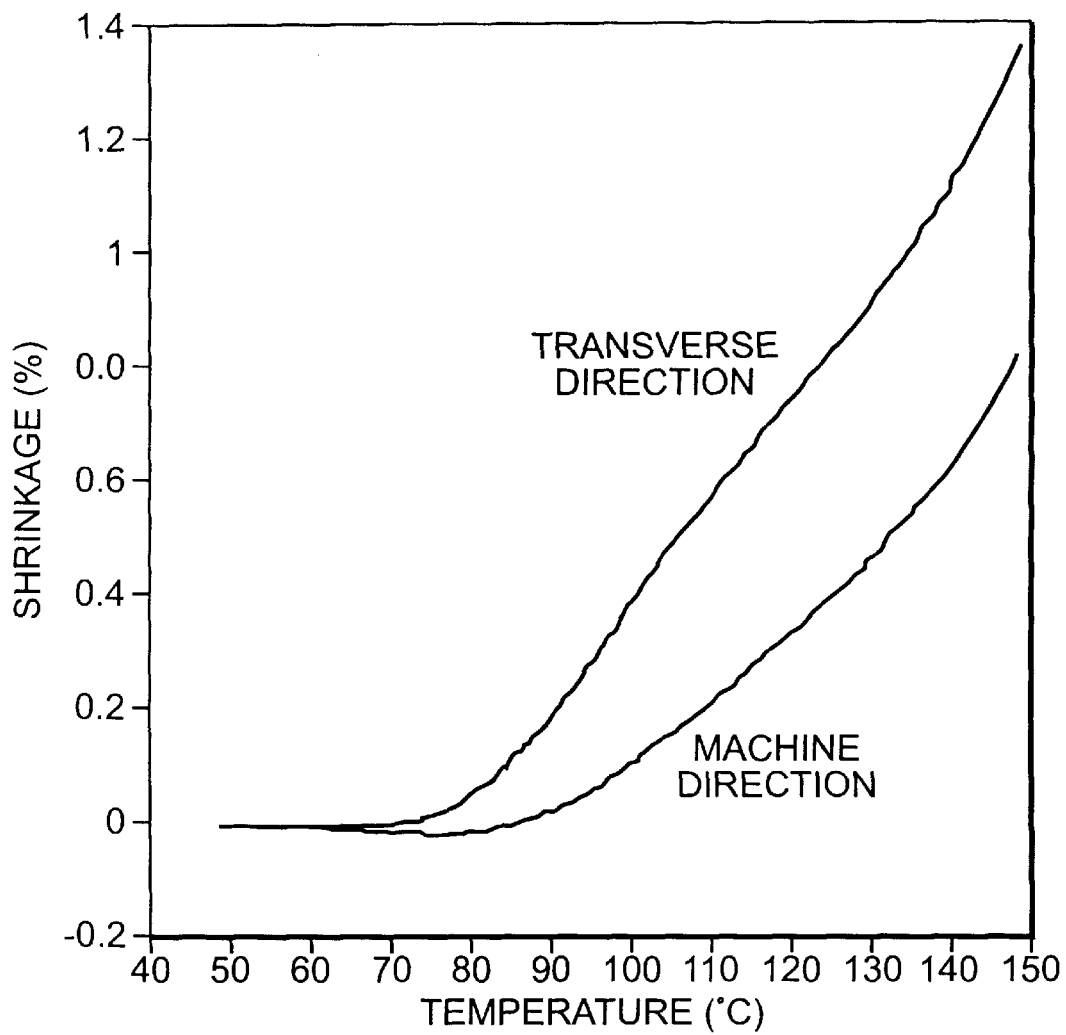
FIG. 9 is a plot of the difference in thermal shrinkage according to sample geometry

The latter two quantities can be integrated with respect to time or temperature, as appropriate, to allow the total length change and length change due to thermal expansion to be determined—results for the temperature range spanning the glass-rubber transition of PET are shown in FIG. 8. The dilatometric $T_g$ of the sample can be estimated by extrapolation of the linear regions of the thermal length change profile above and below the change in thermal expansion coefficient that accompanies devitrification. It is apparent from the total length change curve that some shrinkage begins to occur below this temperature. This effect has been observed by Haworth et al. who used conventional TMA to characterize the shrinkage of oriented PET films. These authors were only able to measure the thermal expansion of the film below $T_g$, whereas the present method permits measurement of this parameter through and above the glass transition region. The difference between the two curves represents the amount of shrinkage due to relaxation of orientation that takes place (i.e. the cumulative integral of f(t,T) in Eq. (2)). Results for film tested along the transverse and machine direction are shown in FIG. 9. There is roughly twice as much shrinkage in the transverse direction, a result which is in agreement with the common manufacturing conditions for this product.

This example shows that the application of modulated-temperature programming to thermomechanical analysis (TMA) allows changes in sample dimensions due to shrinkage arising from relaxation of imposed stresses and conventional thermal expansion to be distinguished. The results for the biaxally oriented PET film of this example show that the method has practical applications for the study of oriented polymers. This approach may also be useful for specimens which soften and flow under the applied load during TMA experiments.

EXAMPLE 2

Figure 10:
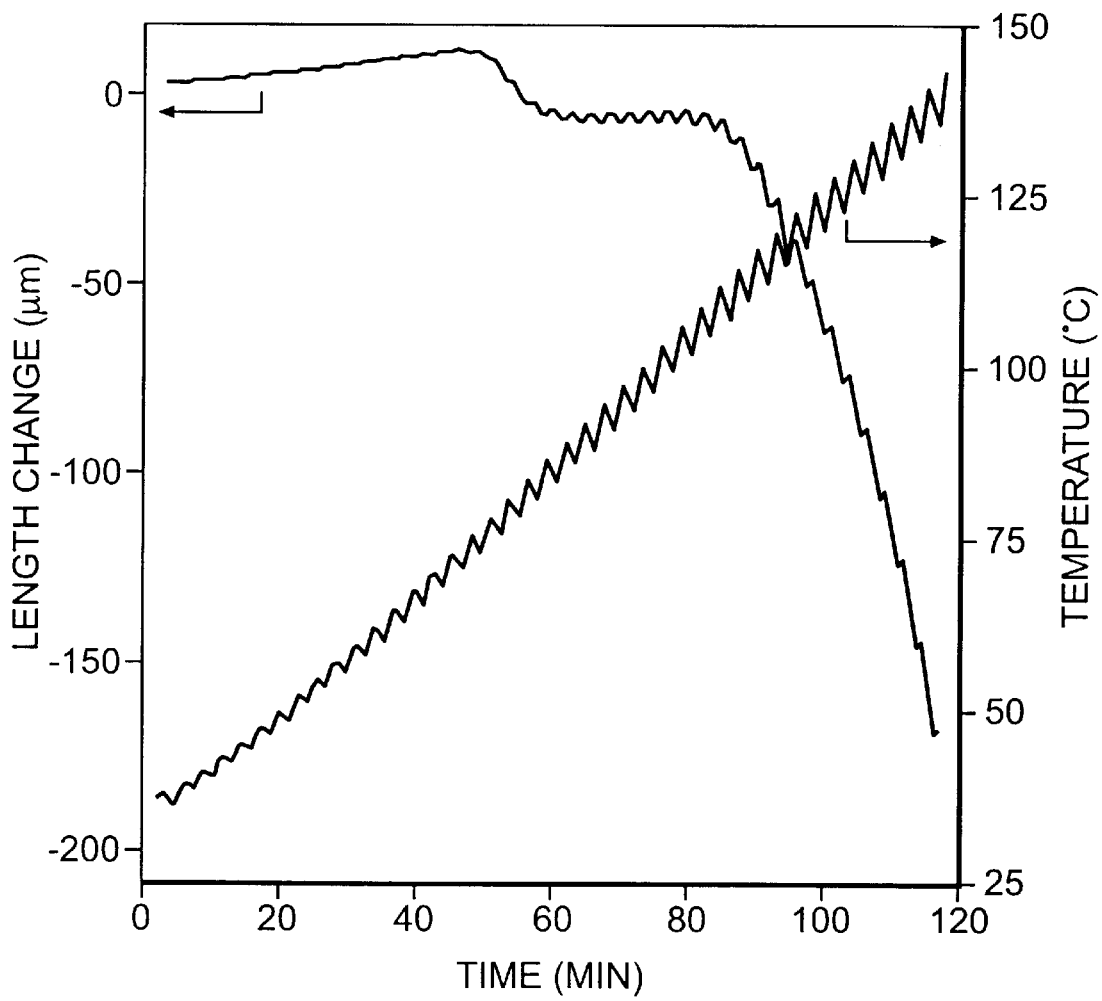
FIG. 10 is a plot of the raw length change and temperature data for the measurement of Example 2.

The second example illustrates the use of the present invention with the TMA configured in the compression configuration shown in FIG. 2. A sample of 3 mm thick clear, unplasticized poly(vinylchloride) was placed beneath a 3 mm diameter flat-ended silica probe under a 200 gm load. Measurements were started at 30 degrees centigrade, followed by a succession of heat/hold/cool/hold stages which served to alternately raise the oven temperature by 5 degrees centigrade at 10 degrees centigrade per minute, followed by a 1 minute isotherm, and then reduce the oven temperature by 2.5 degrees centigrade at the same rate, again followed by a 1 minute isotherm. This cycle was repeated until a temperature of 150 degrees centigrade was reached. Sample length change and temperature were recorded every second. The raw data resulting from this measurement is shown in FIG. 10.

Figure 11:
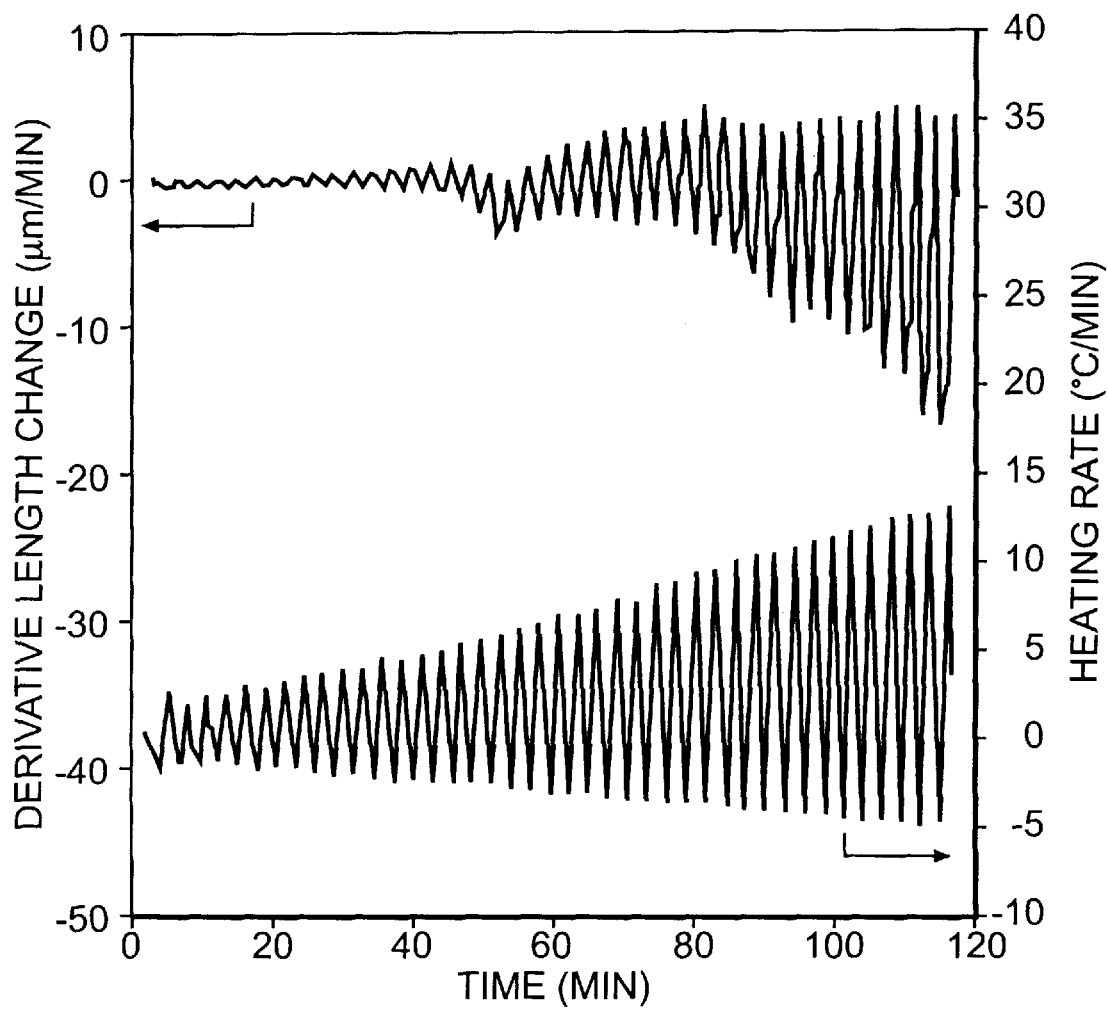
FIG. 11 is a plot of the first derivative of the length change and temperature profiles for the raw data shown in FIG. 10 (Example 2).
Figure 12:
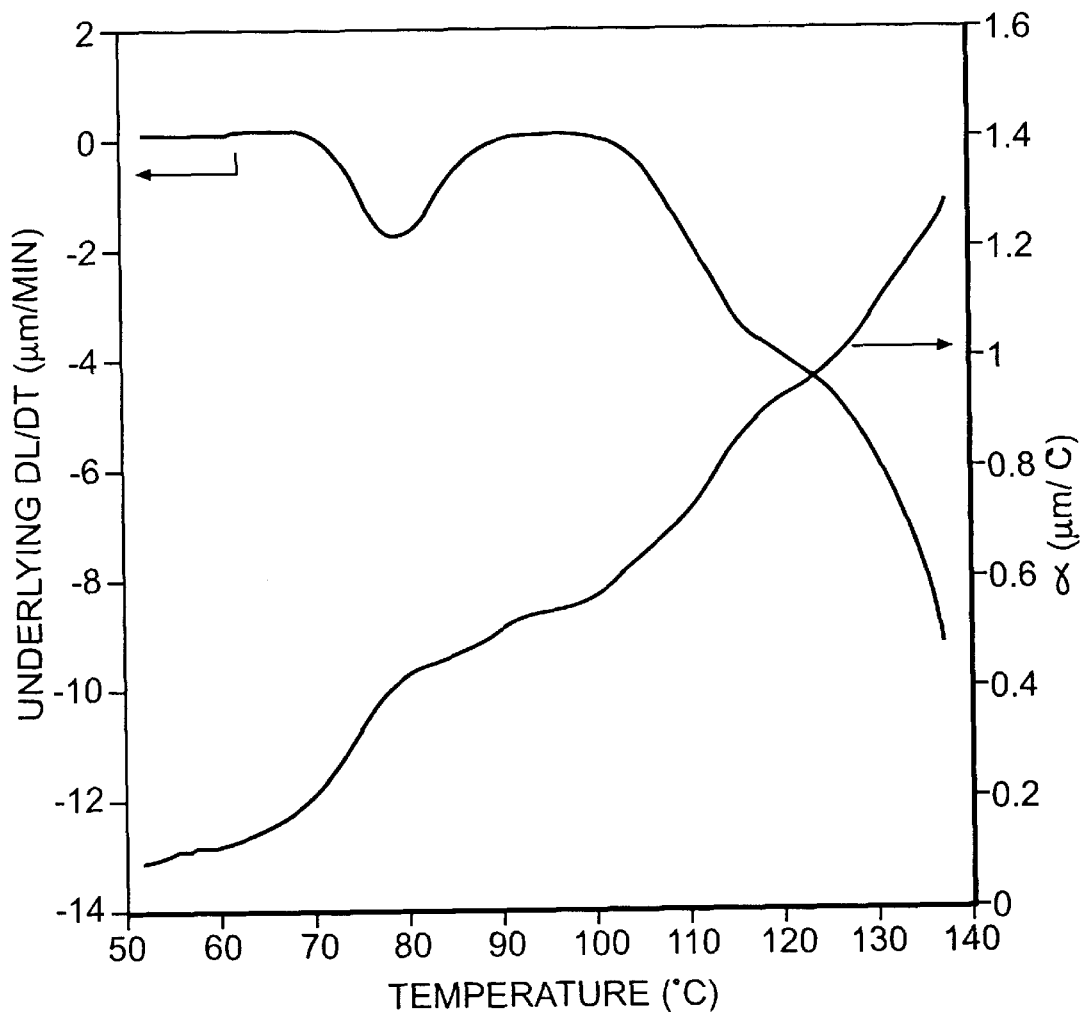
FIG. 12 is a plot of the underlying derivative length change (dL/dt) and thermal expansion coefficient (α) for the raw data of FIG. 10 (Example 2).

FIG. 11 is a plot of the first derivatives of the length change and temperature (dT/dt). The heating rate oscillates about a mean value of 0.91 degrees centigrade per minute, with a period of 165 seconds. Although the heating rate amplitude increased during the measurement (probably due to poor optimization of the temperature controller), the data could be deconvoluted using the method described in U.S. Pat. No. 5,474,385 to Reading (substituting the rate of change of sample length for heat flow). In this case, the phase lag was found to be almost invariant throughout the measurement, and a simpler deconvolution procedure could be used, whereby the underlying rate of change of sample length was found by averaging the length change data over one cycle, and determining the thermal expansion coefficient ($\alpha$) from the amplitude of the oscillating component of the (dL/dt) signal divided by the amplitude of the oscillating heating rate. This plot is shown in FIG. 12.

Figure 13:
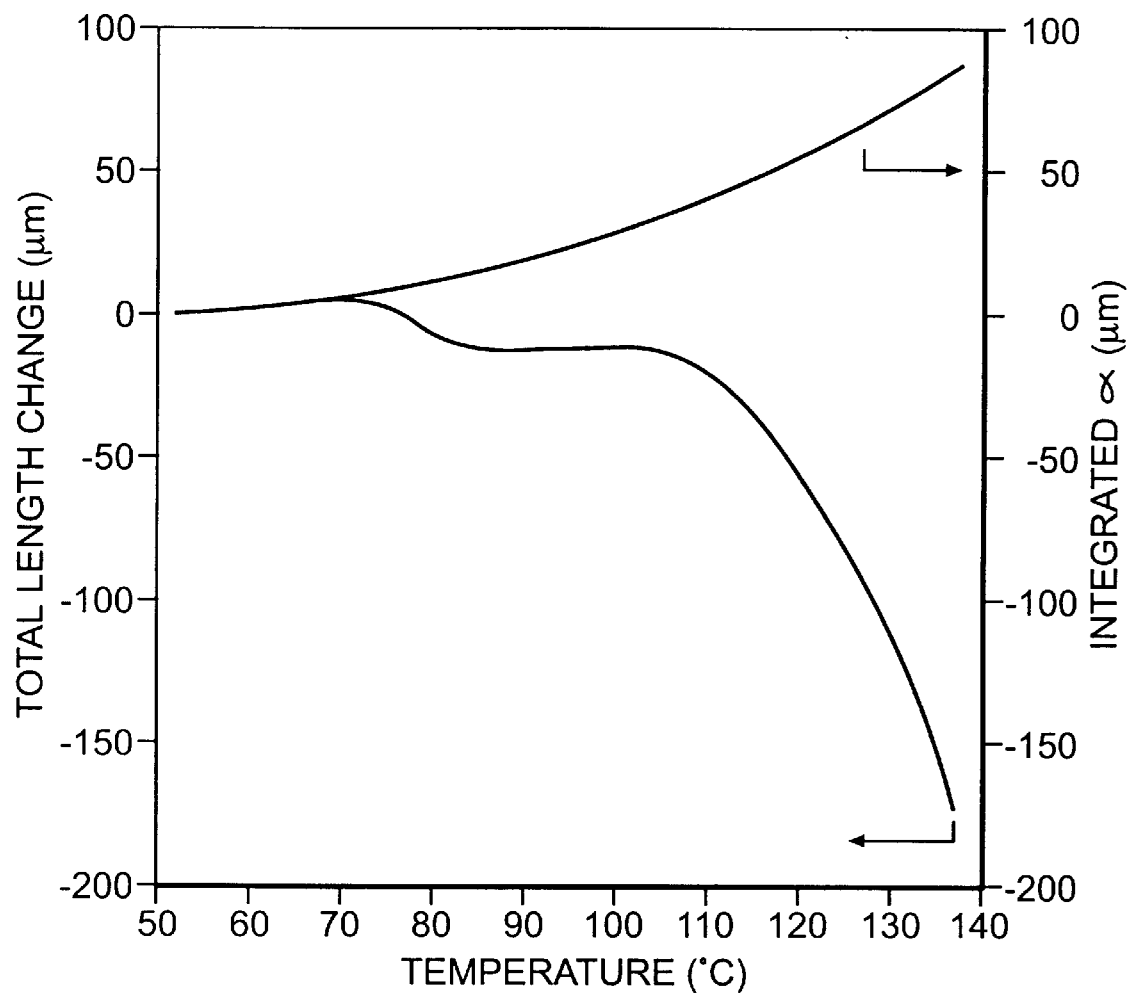
FIG. 13 is a plot of the cumulative integral of the data shown in FIG. 12, showing the total length change and the change in length due to thermal expansion, respectively (integrated α) of the poly(vinylchloride).

These quantities can be integrated with respect to time (for the underlying dL/dt) or temperature (for $\alpha$), as shown in FIG. 13, to allow the total length change and length change due to thermal expansion to be determined. The difference between the two curves represents the amount of penetration of the probe into the sample due to softening of the sample. This difference is therefore representative of the viscoelastic properties of the sample.

Since the heating program exposes the sample to a succession of heat/cool/re- heat cycles, it is possible to separately analyze each part of the temperature profile to study the effect of the thermal history of the sample response (this approach was called "parsing" in U.S. Pat. No. 5,474, 385). Treatment of the data in this manner shows that the bulk of the sample's softening under load occurs during the first heating part of the temperature cycle, and that thermal expansion is largely unaffected by the direction of the temperature change (except in the glass transition region, where the relaxation effects are evident).

This example shows that it is not necessary to employ a constant period, amplitude and underlying heating rate temperature program for modulated TMA measurements. Instead, the course of the temperature profile can be chosen according to the sample response. The technique illustrated in this example may be used to separate the reversible changes that occur due to thermal expansion from irreversible effects that occur when a sample softens under load.

EXAMPLE 3

Calibration

Because the sample temperature is not recorded directly, it generally lags (or leads) the temperature recorded by the apparatus (compare the position of the sample sensor to the sample in FIGS. 1–4 ). This effect can be accounted for by calibration, using the following procedure.

A sample of the material to be tested is measured under the experimental conditions to be used for a temperature region (e.g., room temperature, or alternatively the temperature selected for the start of the measurement) in which no thermal events are expected to occur. In this region, the total and reversing components should provide the same results (because there are no non-reversing thermal events occurring). Because the temperature oscillations measured by the apparatus thermocouple are not completely experienced by the sample, i.e., the temperature oscillations in the sample are "damped" compared to the temperature oscillations measured by the thermocouple (or other temperature sensor), calibration is need for quantitative results.

Figure 14:
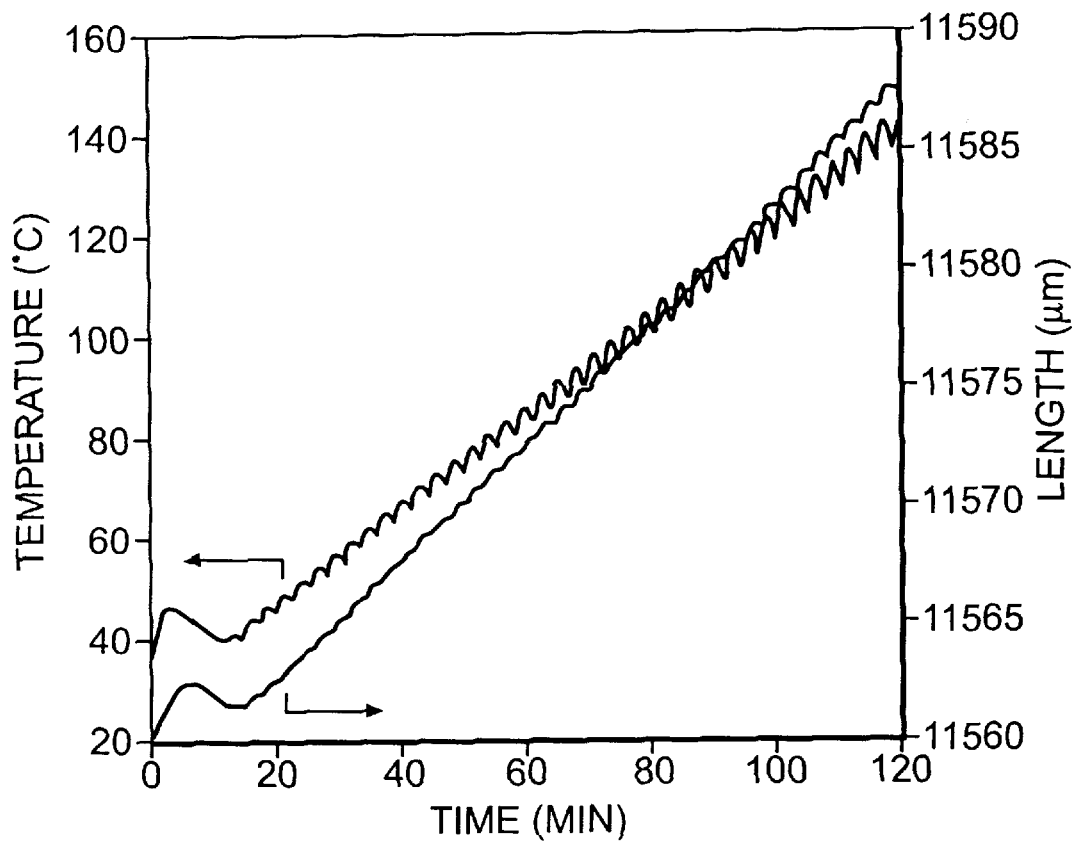
FIG. 14 is a plot of the temperature and length of the aluminum rod, as it is heated according to the temperature program described in Example 3.

FIG. 14 is a plot of the raw data for a 11.56 mm long, 5 mm diameter aluminum rod in the region from about 20 degrees centigrade to 160 degrees centigrade. In this region, aluminum does not experience any thermal events—the only effects are due to the reversible expansion/contraction of the aluminum.

Thus if the oven temperature is given by:

$$T = A[f(t/p) + B \cdot t] + C$$

Where f(t/p) is a periodic function such as a sinusoidal function, A is the amplitude of the temperature oscillation, B is the average heating rate and C is the initial temperature.

The heating rate dT/dt is therefore given by:

$$dT/dt = a[f(t/p)] + B$$

Because the sample temperature leads or lags the temperature measured by the apparatus, the instantaneous heating rate for the sample is given by:

$$DT/dt = A * k[f(t/p)] + B$$

where k is the calibration constant to be determined.

The value of k can be calculated by comparing the rate of length change for the total measurement (i.e., the change in length of the aluminum rod as it is heated from 20 to 160 degrees centigrade) to the reversing rate of length change (essentially, the amplitude of the rate of length change divided by the amplitude of the rate of temperature change). Since there are no thermal events occurring, the two values should be the same, except for effects due to the experimental conditions, such as the relative effectiveness of the transfer of heat from the furnace to the sample and to the thermocouple. The calibration constant k is then given by:

$$k = (\text{reversing rate of length change})/(\text{total rate of length change})$$

As a general rule, this calibration constant is a number between 0 and 1.0.

I claim:

1. A method for analyzing the thermomechanical properties of a sample of material comprising:
   (a) placing the sample of the material in a thermomechanical analyzer;
   (b) raising the temperature of the sample according to a temperature program having an underlying heating rate modulated by a modulation function;
   (c) recording data representative of the change in length of the sample as a function of the temperature recorded by the analyzer; and
   (d) deconvoluting the recorded data to obtain one component data set representative of the reversible component of the change in length of the sample.

2. The method of claim 1, further comprising deconvoluting the recorded data to obtain a second component data set representative of the non-reversible component of the rate of change in the length of the sample.

3. The method of claim 1, further comprising deconvoluting the recorded data to calculate deconvoluted data, and plotting the deconvoluted data to show the separate contributions from the underlying rate of change of sample length and thermal expansion.

4. The method of claim 1, further comprising plotting the cumulative integral of the rate of change of sample length with respect to time.

5. The method of claim 1, further comprising calculating the thermal expansion of the sample, and plotting the cumulative integral of the thermal expansion with respect to temperature.

6. The method of claim 1, comprising measuring the thermal shrinkage of the sample in the transverse direction and in the machine direction, and plotting thermal shrinkage according to sample geometry.

7. A method for analyzing a sample of a material comprising:
   (a) holding a first end the sample in a fixed position in a furnace;
   (b) holding a second end of the sample at a free position in the furnace, and applying a force to the second end of the sample;
   (c) increasing the temperature of the sample using a temperature program characterized by having an underlying rate of change modulated by a modulation function;
   (d) measuring the position of the second end of the sample and the temperature of the sample;
   (e) recording the position of the second end of the sample as a function of the temperature of the sample, and calculating the change in the length of the sample as a function of the temperature of the sample; and
   (f) deconvoluting the change in the length of the sample into at least one component data set.

8. The method of claim 7, wherein the component data set is representative of the reversible component of the change in length of the sample.

9. The method of claim 7, wherein the component data set is representative of the non-reversible component of the change in length of the sample.

10. The method of claim 7, wherein the change in length of the sample is deconvoluted into a first data set representative of the reversible component of the change in length of the sample and a second component data set representative of the non-reversible component of the change in length of the sample.

11. The method of claim 7, further comprising calculating a calibration constant from the ratio of the rate of length change for the total measurement to the reversing rate of length change in a temperature region in which the sample does not experience any thermal events.

12. The method of claim 7, wherein the heating rate amplitude increases during measurement, and the change in the length of the sample is deconvoluted into at least one component data set by averaging the length change data over one cycle, and determining the thermal expansion coefficient from the amplitude of the oscillating component of the thermal expansion divided by the amplitude of the oscillating heating rate.

13. An apparatus for measuring the thermomechanical properties of a sample comprising:
   (a) a furnace comprising means for holding one end of a sample in a fixed position, and means for exerting force on a second end of the sample at a free position;
   (b) a temperature sensor for measuring the temperature of the sample;
   (c) a position sensor for measuring the position of the second end of the sample;
   (d) means for applying a temperature program having an underlying rate of change modulated by a modulation function;
   (e) means for calculating the rate of change of the length of the sample as a function of the temperature of the sample to obtain a raw data set; and
   (f) means for deconvoluting the raw data set into at least one component data set representative of the non-reversible component of the rate of change in length of the sample.

14. The apparatus of claim 13, wherein the furnace comprises a main furnace and a temperature modulation furnace.

15. The apparatus of claim 13, wherein the means for deconvoluting the raw data set into at least one component data set comprises means for calculating the average time, temperature, rate of length change and thermal expansion coefficient for each modulation cycle.

16. The apparatus of claim 13, wherein the raw data set is also deconvoluted into at least one component data set representative of the reversible component of the rate of change in length of the sample.

17. The apparatus of claim 13, further comprising means for plotting the underlying rate of change of sample length and the contribution from thermal expansion.

18. The apparatus of claim 13, further comprising means for plotting cumulative integrals of the change in length with respect to time and the thermal expansion with respect to temperature.

19. An apparatus for measuring viscoelastic properties of a sample comprising:
   (a) a furnace comprising a hard surface upon which the sample can be placed;
   (b) a hard rod;
   (c) means for pressing the hard rod against the surface of the sample;
   (d) a temperature sensor for measuring the temperature of the sample;
   (e) a position sensor for measuring the position of the hard rod;
   (f) means for applying a temperature program having an underlying rate of change modulated by a modulation function;

(g) means for calculating the rate of change of the position of the rod as a function of the temperature of the sample to obtain a raw data set; and (h) means for deconvoluting the raw data set into at least one component data set representative of the non-reversible component of the rate of change in the position of the rod.

20. The apparatus of claim 19, wherein the furnace comprises a main furnace and a temperature modulation furnace.

21. The apparatus of claim 19, wherein the means for deconvoluting the raw data set into at least one component data set comprises means for calculating the average time, temperature, and rate at which the hard rod presses into the sample for each modulation cycle.

22. The apparatus of claim 19, wherein the raw data set is also deconvoluted into at least one component data set representative of the reversible component of the rate of change of the position of the rod.

* * * * *